United States Patent [19]

Johnston et al.

[11] Patent Number: 4,886,501
[45] Date of Patent: Dec. 12, 1989

[54] IMPLANTABLE DEVICE

[75] Inventors: Jimmie T. Johnston, Norwood; Edward J. Sampson, Carlisle, both of Mass.

[73] Assignee: Shiley Infusaid Inc., Norwood, Mass.

[21] Appl. No.: 307,244

[22] Filed: Feb. 6, 1989

Related U.S. Application Data

[63] Continuation of Ser. No. 89,113, Aug. 25, 1987, abandoned.

[51] Int. Cl.⁴ ............................................. A61M 5/32
[52] U.S. Cl. .................................. 604/175; 604/93; 604/283
[58] Field of Search ............... 604/93, 175, 244, 283; 128/1 R, DIG. 26; 623/8

[56]  References Cited
U.S. PATENT DOCUMENTS

| | | | |
|---|---|---|---|
| 3,288,137 | 11/1966 | Lund | 128/DIG. 26 |
| 3,699,956 | 10/1972 | Kibrilakis et al. | 604/175 |
| 3,752,162 | 8/1973 | Newark | 604/93 |
| 4,190,040 | 2/1980 | Schulte | 623/8 |
| 4,230,109 | 10/1980 | Geiss | 604/93 |
| 4,439,188 | 3/1984 | Dennehey et al. | 604/283 |
| 4,459,318 | 7/1984 | Hyans | 604/175 |
| 4,464,178 | 8/1984 | Dalton | 604/174 |
| 4,490,137 | 12/1984 | Moukheibir | 604/175 X |
| 4,543,088 | 9/1985 | Bootman et al. | 604/93 |
| 4,578,063 | 3/1986 | Inmann et al. | 604/175 |
| 4,581,020 | 4/1986 | Mittleman | 604/175 |
| 4,634,443 | 1/1987 | Haber | 128/1 R |
| 4,645,495 | 2/1987 | Vaillancourt | 604/180 |
| 4,673,394 | 6/1987 | Fenton, Jr. et al. | 604/175 |
| 4,692,146 | 9/1987 | Hilger | 604/93 |
| 4,695,273 | 9/1987 | Brown | 604/173 |
| 4,704,103 | 11/1987 | Stober et al. | 604/93 |
| 4,710,167 | 12/1987 | Lazorthes | 604/175 |
| 4,710,174 | 12/1987 | Moden et al. | 604/175 |

FOREIGN PATENT DOCUMENTS

| | | |
|---|---|---|
| 0119596 | 9/1984 | European Pat. Off. . |
| 0134745 | 3/1985 | European Pat. Off. . |
| 3528878 | 2/1987 | United Kingdom ............... 604/280 |

Primary Examiner—John D. Yasko
Attorney, Agent, or Firm—Sughrue, Mion, Zinn, Macpeak & Seas

[57] ABSTRACT

A device that is implantable to provide access to multiple body sites for the administration or withdrawal of fluids. A hollow port has a self sealing septum on one end and an outlet at an opposite end. A catheter is connected to the outlet. The septum and outlet are positioned to be substantially in-line.

20 Claims, 2 Drawing Sheets

IMPLANTABLE DEVICE

This is a continuation of application Ser. No. 089,113, filed Aug. 25, 1987, now abandoned.

BACKGROUND OF THE INVENTION

This invention relates to an implantable device and in particular, to a vascular access device that is implanted subcutaneously.

Within the prior art, a variety of implantable access devices are known. Typical is the commercially available INFUSAID Infuse-A-Port TM. These techniques of providing access via a various implantable device include percutaneous catheters, implantable ports having access to a port at a perpendicular angle to the skin and direct access with a needle. Thus, in the case of the commercially available Infuse-A-Port TM, a base having an inlet located under the skin having an access outlet perpendicular to the skin line. The catheter thus extends at a right angle to the direction of needle access to the port's inlet.

Materials which are used in these devices generally include various plastics such as PVC, teflon, polyethylene, polypropylene, polyurethane, polycarbonate, polyethersulfone, polysulfone, polyolefin, nylon and the like. Additionally, silicone rubber, stainless steel and titanium are used.

A hallmark characteristic of all previous techniques of access utilizing implantable ports is a requirement that a needle be placed into the port septum at a 90° angle to the outlet catheter. This is acceptable for bolus injections or infusions over brief periods of time. However, for longer infusions or for continuous infusions with these ports, a right angle needle is required to allow for the hub of the needle to be parallel with the skin. This is required to permit anchoring of the needle to the body during infusions.

Another disadvantage with such prior art devices is that they require minor but, a distinct surgical procedure for implantation. That is, the size of the base is such that a significant incision is required for implantation. Moreover, given the size of the base, implantation is required in specific portions of the body, for example, the chest and stomach area that can physically support and house the port without protuberances or discomfort to the patient.

Given these deficiencies of prior art devices, it is an object of this invention to define an implantable access device for humans having a low profile capable of implantation in a variety of bodily locations, which provides access to multiple body sites.

Yet another object of this invention is to define a low, acute angle implantable port which provides access to multiple body sites for research purposes in animals.

Yet another object of this invention is to provide an acute angle implantable device providing access to multiple body sites in small patients, such as infants, neonates and children.

A further object of this device is to provide for an implantable port which has a reduced size such that implantation can be carried out minimizing both the surgical procedure time and size of the incision.

These and other objects of this invention are achieved by means of an acute angle port having a port body holding a self-sealing septum. The port body has grooves, wings, or flaps which allow for suturing the port to subcutaneous tissue. The self-sealing septum in accordance with this invention has the ability to be connected to various catheters such that when coupled, the port provides direct facile access to the catheter. This direct access to the catheter allows for catheter tip placement or for the management of blockages in the catheter. Such is extremely difficult in the context of ports which are disposed at right angles to the catheter output.

These and other objects of this invention are set forth herein by reference to the attached drawings and the descriptions of the preferred embodiments which follows.

DESCRIPTION OF THE PREFERRED EMBODIMENTS

Figure 1:
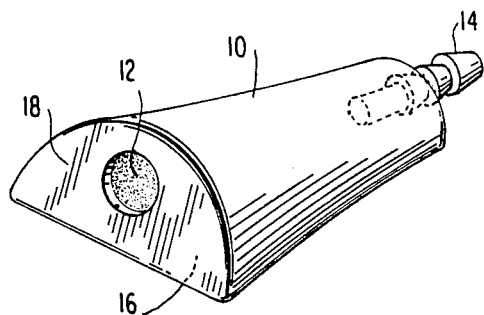
FIG. 1 is a schematic perspective view of a first embodiment of an implantable port in accordance with this invention.

Referring now to FIG. 1, a first embodiment of the implantable port of this invention is illustrated. The port comprises a body member 10 having a self-sealing septum 12 and an outlet connector 14 to which a suitable catheter is mounted. As illustrated in FIG. 1, the port has a generally flat base area 16 with an inclined face 18 into which the septum is placed. The septum provides a small diameter target, typically 0.15–0.20 inches. The overall length of the device from the front face to the tip of the connector is in the range of one inch. The overall height of the device from the flat base 16 to the tapered top portion is at a maximum approximately 0.38 inches. The port and the connector is manufactured from a bicompatible material. Materials of choice for the port are silicone rubber and various plastics such as PVC, teflon, polyethylene, polypropylene, polyurethane, polycarbonate, polyethersulfone, polysulfone, polyolefin, nylon, and the like. The connecter is preferably a metallic member made of stainless steel or titanium. The entire device can be made of one piece, for example a suitable metal.

As illustrated in FIG. 1, the front face 18 is inclined so that access to the self-sealing septum 12 is axially aligned with the connecter 14. This is in contrast to prior art systems wherein normal access to the septum would be disposed at a right angle, that is perpendicular to the outlet connector to the catheter.

Given the low profile of the device, implantation in areas with limited subcutaneous tissue such as forearms, scalp and neck area, infants and children and their appendages is possible.

Figure 2:
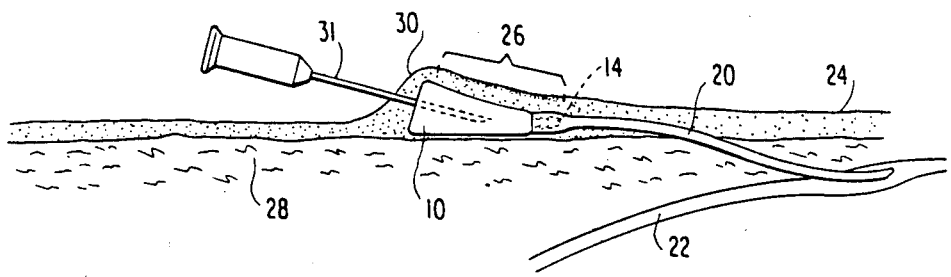
FIG. 2 is a schematic illustration showing the placement of the implantable port of this invention subcutaneously with the catheter extended into a blood vessel.

Referring now to FIG. 2, the device of FIG. 1 including the catheter is shown implanted. Specifically, the port 10 has coupled to it a catheter 20 of suitable length. The catheter is force-fitted onto the connecter 14 having its free end lanced into a suitable blood vessel 22. The catheter made from a biocompatible material such as silicone rubber or polyurethane and depending on the application may have a radiopaque material added. The device is implanted under the skin 24 by making a small localized incision 26. The incision is shallow and does not involve incursion into underlying muscle tissue 28. Given the low profile of the device, a small protrusion 30 in the skin is present but such is not obtrusive or acts in any way as an impediment to normal functioning at the implantation site.

Access to the device 10 is by means of a needle 32. As can be seen from FIG. 2. The needle penetrates the skin at the protrusion 30 directly into the target or port zone 12 and is in line with the outlet 14. A major advantage of this system is that given the in-line nature of the septum, outlet and catheter access to the catheter tip for management of blockages is possible. This also allows the use of straight needles as illustrated in FIG. 2 for access to the port since entry is generally parallel to the skin line. Moreover, if it is necessary to pass a guide wire through the port and into the catheter, such can be done without making any significant bends. The ability to pass a guide wire or other appropriate device into the catheter after implantation provides a significant advantage in terms of clearing the catheter or importantly, initially placing the catheter tip at an appropriate location within the body. Such is extremely difficult in prior art right angle systems.

As can be appreciated from FIG. 2, the use of a straight needle provides a material advantage over prior techniques. Additionally, if the needle is required to be taped down then, it is a simple matter of affixing the needle when in contact with the septum to the skin yet not substantially immobilize the patient. Thus, for example, if the port 10 is implanted in an arm the needle can simply be taped or strapped in place thereby anchoring the needle to the body during infusion or injections requiring a period of time.

Figure 3:
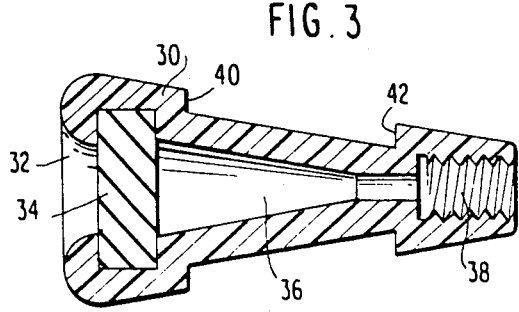
FIG. 3 is a schematic cut-away view of a second embodiment of this invention.

FIG. 3 illustrates a second embodiment of an in-line port in accordance with this invention. As illustrated in FIG. 3, the port is generally circular and comprises the body member 30 having an opening 32. A self-sealing septum 34 is placed into the body 30 to close off the opening 32 and provide a suitable target. The port has a hollow portion 36 generally axially in line with the self-sealing septum 34. The hollow portion serving as a reservoir terminates into a zone which is tapped, that is area 38 to allow for the catheter connection. The overall length of the device is in the range of 0.75-1.0 inches. The maximum diameter is in the range of 0.4 inches. The exposed area, that is opening 32 is in the range of 0.25 inches. As in the case of the first embodiment a variety of materials may be used, such as polysulfone.

The device of FIG. 3 has two annular shoulders 40 and 42. These shoulders provide zones for holding a tie-down element (not illustrated) around the device.

Figure 4:
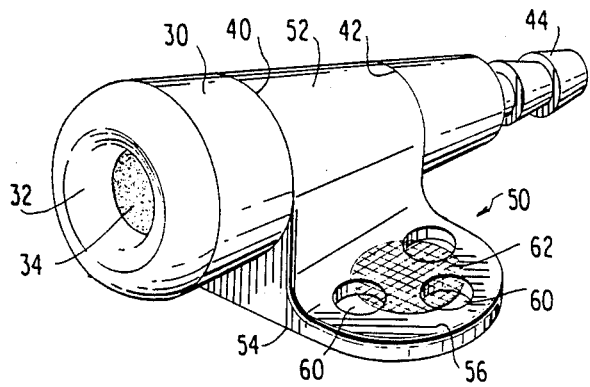
FIG. 4 is a perspective view of the embodiment of FIG. 3 utilizing a separately molded tie-down element.
Figure 5:
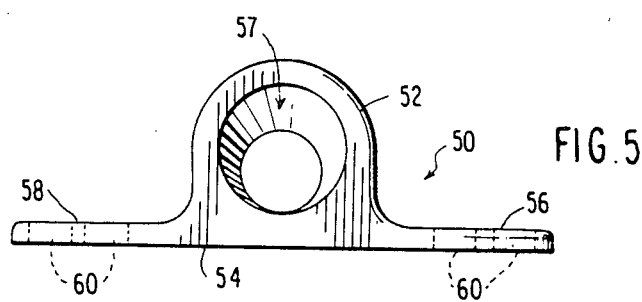
FIG. 5 is an end view of the tie-down element of FIG. 4.

Referring now to FIGS. 4 and 5, a perspective vein of the port illustrated in FIG. 3 is depicted. The numeral is used to identify the same aspects of the embodiment of FIG. 3 are used in FIGS. 4 and 5. Additionally, FIG. 4 illustrates the connecter 44 for the catheter coupled to the outlet portion of the port, that is, screwed into the zone 38 and having a series of annular barbs or serrations upon which the catheter is fixed.

As illustrated in FIG. 5 the tie-down comprises a separate element which is a separately molded material. Specifically, the tie-down 50 comprises a body portion 52 inclined to the horizontal relative to a base portion 54. Through an opening 56, the device 30 is inserted such that as illustrated in FIG. 4 the rear portion of the device at shoulder 30 butts against the rear portion of the tie-down while the front shoulder 40 butts against the inclined front wall. Consequently, when snapped into position the tie-down inclines the port and provides a pair of extending "wings" for purposes of suturing the device into place. Various techniques of suturing the wings 56, 58 may be used. As illustrated in FIG. 4, a series of holes 60 can allow for sutures to be stitched through and around each of the wings. Alternatively, a zone of exposed dacron fabirc 62 may be used to provide a confined anchoring area on each of the wing surfaces.

Figure 6:
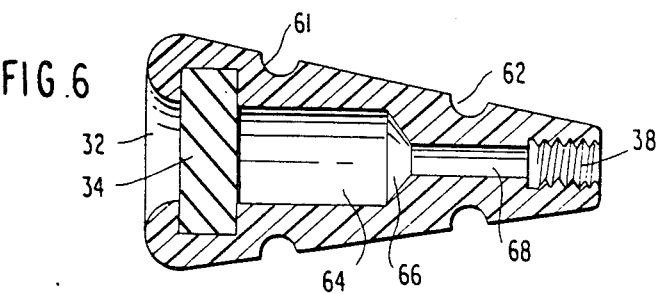
FIG. 6 is a schematic cut-away side view of a third embodiment of this invention.

Referring now to FIG. 6, a third preferred embodiment of this invention is illustrated. The embodiment of FIG. 6 departs from that illustrated in FIG. 3 in that the device while retaining its generally truncated conical form eliminates the shoulder zones 40 and 42. In its place, two annular rings 60 and 62 are employed. These provide two suture hold down locations. Another variation is that the hollow area 64 in the embodiment of FIG. 6 is generally rectangular and has a truncated zone 66 coupling a straight in-line portion 68 to the hollow area 64. This serves as a guide for the needle, it being understood that the needle would generally terminate in the zone 64 providing direct fluid access to the catheter. The barbed connector which would be screwed into the device and the threaded portion 38.

Figure 7:
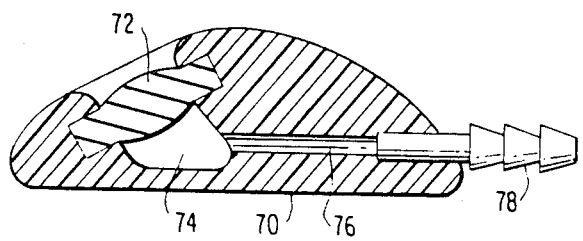
FIG. 7 is a schematic cut-away side view of a fourth embodiment of this invention.

Referring now to FIG. 7, a fourth embodiment of this invention is depicted. In FIG. 7, the device comprises a generally squat body portion 70 having a self-sealing septum 72 embedded therein. The septum 72 is inclined relative to the horizontal flat bottom portion of the device and has a cavity portion 74 defined within the body 70. An outlet hollow port 76 is in fluid communication with an external connector piece 78. The connector piece is force-fitted or the like into the body portion 70 and serves as the connector between the port and the catheter. The body portion may be made of polysulfone or the like and, as illustrated in FIG. 7 has a very low profile. Needle access is provided at a shallow, acute angle to the self-sealing septum 72. The device is anchored in place by through-holes, wings or the like which are not illustrated.

It is apparent that while multiple embodiments of this invention have been illustrated, various other modifications can be made without departing from the essential scope of the invention. A key aspect is the geometry of the device so that straight needles can be used with the device implanted at a very shallow implantation site within an arm, the neck area or the like. Such is considered a material advantage over prior art systems which must be implanted in the torso given their overall size and geometry.

Having described my invention I claim:

1. A body implantable access device comprising; a hollow port, said port having an inlet an outlet and an infusion chamber therebetween, a self sealing septum disposed in and covering said inlet, and said self-sealing septum positioned on said port at substantially a right angle to said outlet such that a needle puncturing said septum will be substantially in line with said outlet.

2. The implantable device of claim 1 further comprising means to mount a catheter at said outlet and a flexible catheter mounted on said means to mount a catheter to provide fluid access to a portion of the body in which said device is implanted.

3. The implantable device of claim 2 wherein said means to mount a catheter comprises a hollow connector one end of which is inserted into said outlet of said port and the other end having annular barbs engaging said catheter.

4. The implantable device of claim 1 further comprising means to anchor said port subcutaneously at an angle substantially parallel with the skin line at the implantation site.

5. The implantable device of claim 4 wherein said means to anchor comprises first and second shoulder portions provided on said port, said shoulder portions extending circumferentially around said port.

6. The implantable device of claim 4 wherein said means to anchor comprises first and second circumferential recesses provided on said port.

7. The implantable device of claim 4 wherein said means to anchor comprises a tie-down member having means to mount said body, said tie-down member further including a flat portion defining a sutures area.

8. The implantable device of claim 7 wherein said flat portion includes a series of through-holes for passing sutures.

9. The implantable device of claim 7 wherein said flat area includes a fabric mesh for passing sutures.

10. The implantable device of claim 1 wherein said self sealing septum is angled at a shallow acute angle with respect to said outlet.

11. A body implantable device providing access to an internal portion of a living body for the administration and withdrawal of fluids comprising:
a hollow port made of a biocompatible material, said port having wall portions defining an inlet, an outlet and an infusion chamber therebetween, a self sealing septum member positioned to cover said inlet at substantially a right angle to said outlet to provide a target for a needle used in the administration and withdrawal of fluids, said infusion chamber located upstream of said outlet and blocked from the inlet by said self-sealing septum, and said self sealing septum oriented in said inlet such that a needle passing through said system will stop in said infusion chamber area and will be substantially in line with said outlet.

12. The implantable device of claim 11 further comprising means to mount a catheter at said outlet and a flexible catheter mounted on said means to mount a catheter to provide fluid access to a portion of the body in which said device is implanted.

13. The implantable device of claim 12 wherein said means to mount a catheter comprises a hollow connector one end of which is inserted into said outlet of said port and the other end having annular barbs engaging said catheter.

14. The implantable device of claim 11 further comprising means to anchor said port subcutaneously at an angle substantially parallel with the skin line at the implantation site.

15. The implantable device of claim 14 wherein said means to anchor comprises first and second shoulder portions provided on said port, said shoulder portions extending circumferentially around said port.

16. The implantable device of claim 14 wherein said means to anchor comprises first and second circumferential recesses provided on said port.

17. The implantable device of claim 14 wherein said means to anchor comprises a tie-down member having means to mount said body, said tie-down member further including a flat portion defining a sutures area.

18. The implantable device of claim 17 wherein said flat portion includes a series of through-holes for passing sutures.

19. The implantable device of claim 17 wherein said flat area includes a fabric mesh for passing sutures.

20. The implantable device of claim 11 wherein said self sealing system is angled at a shallow acute angle with respect to said outlet.

* * * * *